(12) United States Patent
Krasnow (10) Patent No.: US 10,488,937 B2
(45) Date of Patent: Nov. 26, 2019

(54) DOPPLER ULTRASOUND PROBE FOR NONINVASIVE TRACKING OF TENDON MOTION

(71) Applicant: Verily Life Sciences LLC, Mountain View, CA (US)

(72) Inventor: Benjamin David Krasnow, Mountain View, CA (US)

(73) Assignee: Verily Life Sciences, LLC, Mountain View, CA (US)

( * ) Notice: Subject to any disclaimer, the term of this patent is extended or adjusted under 35 U.S.C. 154(b) by 670 days.

(21) Appl. No.: 15/221,303

(22) Filed: Jul. 27, 2016

(65) Prior Publication Data
US 2017/0055938 A1    Mar. 2, 2017

Related U.S. Application Data

(60) Provisional application No. 62/210,853, filed on Aug. 27, 2015.

(51) Int. Cl.
*G06F 3/01* (2006.01)
*A61B 8/08* (2006.01)
(Continued)

(52) U.S. Cl.
CPC .............. *G06F 3/017* (2013.01); *A61B 5/681* (2013.01); *A61B 8/085* (2013.01); *A61B 8/4227* (2013.01);
(Continued)

(58) Field of Classification Search
CPC ....... A61B 8/085; A61B 8/4227; A61B 5/681; A61B 8/467; A61B 8/488; A61B 8/4483; A61B 8/58; G06F 3/017; G06F 3/014
See application file for complete search history.

(56) References Cited

U.S. PATENT DOCUMENTS 5,818,359 A    10/1998  Beach
2004/0024312 A1*  2/2004  Zheng ................. A61B 5/1038
                                                            600/437
(Continued)

FOREIGN PATENT DOCUMENTS

CA        2326542 A1    4/2001
WO        0076400 A1   12/2000

OTHER PUBLICATIONS

International Search Report and Written Opinion of International Application No. PCT/US2016/044389 dated Oct. 19, 2016.
(Continued)

*Primary Examiner* — Premal R Patel
(74) *Attorney, Agent, or Firm* — McDonnell Boehnen Hulbert & Berghoff LLP (57) ABSTRACT

Systems and methods for generating an input to a computing device based, at least in part, on movement data generated by one or more ultrasonic transducers are described herein. An example system may include at least one ultrasonic transducer configured to be mounted to a body surface that is proximate to at least one subsurface tendon, and a controller operably coupled to the at least one ultrasonic transducer. When mounted to a body surface, the at least one ultrasonic transducer is configured to detect movement of the at least one subsurface tendon. The controller is configured to operate the at least one ultrasonic transducer to generate movement data based on detected movement of the at least one subsurface tendon, and generate an input to a computing device based, at least in part, on the generated movement data.

20 Claims, 5 Drawing Sheets

(51) Int. Cl.
*A61B 8/00* (2006.01)
*A61B 5/00* (2006.01)

(52) U.S. Cl.
CPC ............ *A61B 8/4483* (2013.01); *A61B 8/467* (2013.01); *A61B 8/488* (2013.01); *A61B 8/58* (2013.01); *G06F 3/014* (2013.01)

(56) References Cited

U.S. PATENT DOCUMENTS

| | | | | |
|---|---|---|---|---|
| 2012/0172682 | A1* | 7/2012 | Linderman | A61B 5/0476 600/301 |
| 2013/0211843 | A1* | 8/2013 | Clarkson | G06F 3/017 704/275 |
| 2015/0323998 | A1* | 11/2015 | Kudekar | G06F 1/163 345/156 |
| 2016/0378193 | A1* | 12/2016 | Camacho Perez | G06F 3/017 345/156 |
| 2017/0052596 | A1* | 2/2017 | Li | G06K 9/00355 |

OTHER PUBLICATIONS

Kelly J. Stegman, "Towards Detection of User-Intended Tendon Motion with Pulsed-Wave Doppler Ultrasound for Assistive Hand Exoskeleton Applications", M.A.Sc. Thesis, 2009.

* cited by examiner

DOPPLER ULTRASOUND PROBE FOR NONINVASIVE TRACKING OF TENDON MOTION

CROSS-REFERENCE TO RELATED APPLICATION

This application claims priority to U.S. Provisional Patent Application No. 62/210,853, filed Aug. 27, 2015, which is hereby incorporated by reference in its entirety.

BACKGROUND

Unless otherwise indicated herein, the materials described in this section are not prior art to the claims in this application and are not admitted to be prior art by inclusion in this section.

The standard computer keyboard is the predominant way to enter text and information into a computer system. However, a full-size keyboard may not be suitable for use in mobile computing devices such as smart phones, watches, head-mountable devices, and tablets, where portability and small size may be desired. Typically, in mobile devices, a keyboard can be represented in a miniaturized form on a touchscreen, or computer inputs may be made through a limited number of input actions, such as with a reduced number of multi-function buttons. These means of interfacing with mobile devices have limitations. Therefore, providing mobile computing device users with the ability to easily input long passages of text into a smart phone, for example, without using a full size keyboard, could change the way that people use computers.

In addition to the standard keyboard, other means of generating inputs, such as text, into a computer system are currently in use. For example, some smart phones and computer systems utilize a camera to identify user gestures for computer input. However, this technique can be prone to background distractions and occlusion, and may not be effective in adverse lighting conditions. In addition, touchscreen devices allow for various user inputs that may not be limited to entering alphanumeric characters on a keyboard. These devices, however, detect user contact with the surface of the device, and are typically limited to 2D gestures.

SUMMARY

Systems and methods for ultrasonically detecting tendon movement and generating one or more inputs into a computer system therefrom are disclosed herein. A least one ultrasonic transducer mounted to a body surface generates movement data using Doppler ultrasound to detect movement of one or more subsurface tendons. Using the generated movement data, a controller generates one or more inputs into a computer system, such as a smart phone or other mobile computing device.

Embodiments of the present disclosure provide a system including: (1) at least one ultrasonic transducer configured to be mounted to a body surface that is proximate to at least one subsurface tendon, wherein the at least one ultrasonic transducer is configured to detect movement of the at least one subsurface tendon when so mounted; and (2) a controller operably coupled to the at least one ultrasonic transducer, and wherein the controller is configured to perform operations comprising: (a) operating the at least one ultrasonic transducer to generate movement data based on detected movement of the at least one subsurface tendon; and (b) generating an input to a computing device based, at least in part, on the generated movement data.

Further embodiments of the present disclosure provide a method including: (1) generating, by at least one ultrasonic transducer, movement data based on detected movement of at least one subsurface tendon, wherein the at least one ultrasonic transducer is configured to be mounted to a body surface that is proximate to the at least one subsurface tendon, and wherein the at least one ultrasonic transducer is configured to detect movement in the at least one subsurface tendon when so mounted; and (2) generating, by a controller, an input to a computing device based, at least in part, on the generated movement data.

Further embodiments of the present disclosure provide a non-transitory computer readable medium having stored therein instructions executable by a processor to cause a controller to perform operations including: (1) operating at least one ultrasonic transducer to generate movement data based on detected movement of at least one subsurface tendon, wherein the at least one ultrasonic transducer is configured to be mounted to a body surface that is proximate to the at least one subsurface tendon, and wherein the at least one ultrasonic transducer is configured to detect movement in the at least one subsurface tendon when so mounted; and (2) generating an input to a computing device based, at least in part, on the generated movement data.

These as well as other aspects, advantages, and alternatives, will become apparent to those of ordinary skill in the art by reading the following detailed description, with reference where appropriate to the accompanying drawings.

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

In example embodiments, a system for generating user inputs into a computer system by noninvasively detecting motion of tendons in a user's hand using Doppler ultrasound and reconstructing the user's gesture based on the detected tendon movement is provided. The system may include a wristwatch-style device that includes an ultrasound transducer. Positioning the device above the carpal tunnel allows the ultrasound transducer to monitor the motion of flexor and/or extensor tendons that control finger movement. The wrist-mounted device could also be a computer (smart watch). While a wrist-mounted device is discussed herein, this device could be adapted to other body locations to sense foot, arm, or any other movement.

One benefit of a wearable system for monitoring tendon motion is that complex gestures can be detected without the user interacting with a touchscreen or handling a device. This wearable system may offer an effective way to provide a human-computer interface for mobile computing devices. While other means for noninvasively measuring tendon movement, such as electrical monitoring of muscles, exist, these other known techniques may not provide the same resolution and robustness as gesture detection by Doppler ultrasound.

In the case of a system designed to monitor finger motion, the input device can monitor the movement of each tendon in the carpal tunnel region of the hand. One way to accomplish this is to use pulsed Doppler ultrasound with a phased array of transducers. This technique is currently used in some medical devices to image bodily structures beneath the skin. In another approach, a pair of transducers may be used to detect movement of each tendon being monitored. A wearer of the device may be instructed, via a user interface, to move a specified finger at a specified time and each pair of ultrasound transducers monitors movement within the field of view of the device. The signals from each pair of transducers can be compared to the instructed finger motion to develop a mapping that assigns how a combination of ultrasound signals indicates a specific finger movement.

It should be understood that the above embodiments, and other embodiments described herein, are provided for explanatory purposes, and are not intended to be limiting.

II. Example Systems and Devices

Figure 1A:
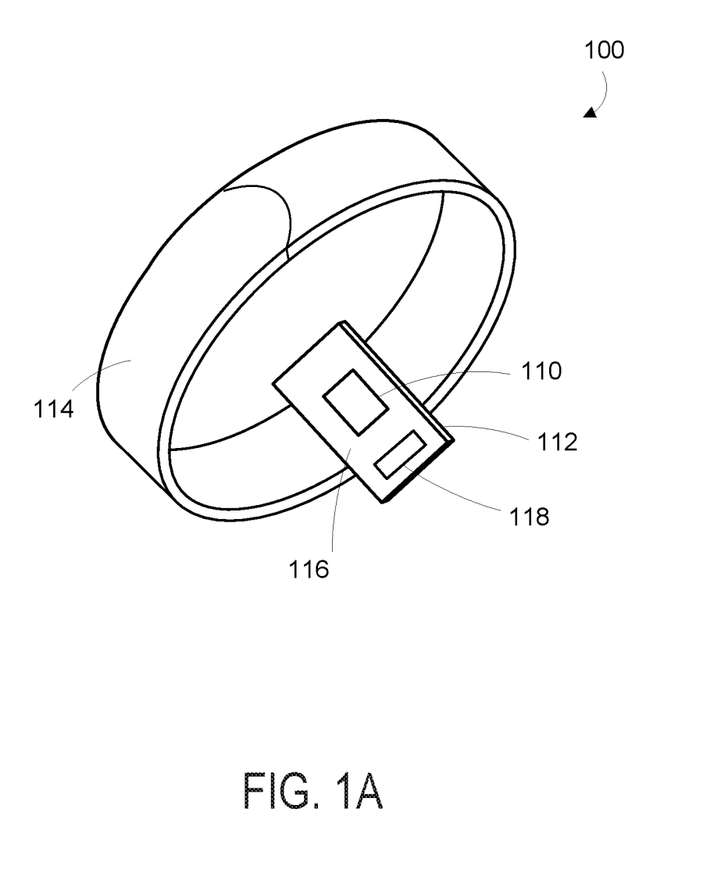
FIG. 1A illustrates an example wearable device including at least one ultrasonic transducer.

FIG. 1A illustrates a wearable device 100, including at least one ultrasonic transducer 110 configured to detect tendon movement. The term "wearable device," as used in this disclosure, refers to any device that is capable of being worn at, on or in proximity to a body surface, such as a wrist, ankle, waist, chest, or other body part. In particular, the wearable device may be positioned on a portion of the body proximate to one or more subsurface tendons. The at least one ultrasonic transducer 110 may be provided in or on a housing 112, the inner face 116 of which may be placed in close proximity to the skin or tissue, but need not be touching or in intimate contact therewith. In some cases, an acoustic coupling material may be positioned between the housing 112 and the skin. A mount 114, such as a belt, wristband, ankle band, etc. can be provided to mount the housing 112 at, on or in proximity to the body surface. The mount 114 may prevent the wearable device from moving relative to the body to reduce measurement error and noise. In one example, shown in FIGS. 1A-1C, the mount 114, may take the form of a strap or band that can be worn around a part of the body.

A communication interface 118 may also be disposed on or within housing 112 for transmitting or receiving data from a remote device, such as, via a communication network. In one embodiment, the communication interface 118 includes a wireless transceiver for sending and receiving communications to and from a remote device. In further embodiments, the communication interface 118 may include any means for the transfer of data, including both wired and wireless communications. For example, the communication interface may include a universal serial bus (USB) interface or a secure digital (SD) card interface. The communication network may be any one of may be one of: a plain old telephone service (POTS) network, a cellular network, a fiber network and a data network. The remote device may include any type of computing device that is remote from the wearable device 100, such as a server, a cloud computing network, a mobile computing device, a personal computing device, etc. As will be explained further below, the remote device may be provided as or may include a controller.

Figure 1B:
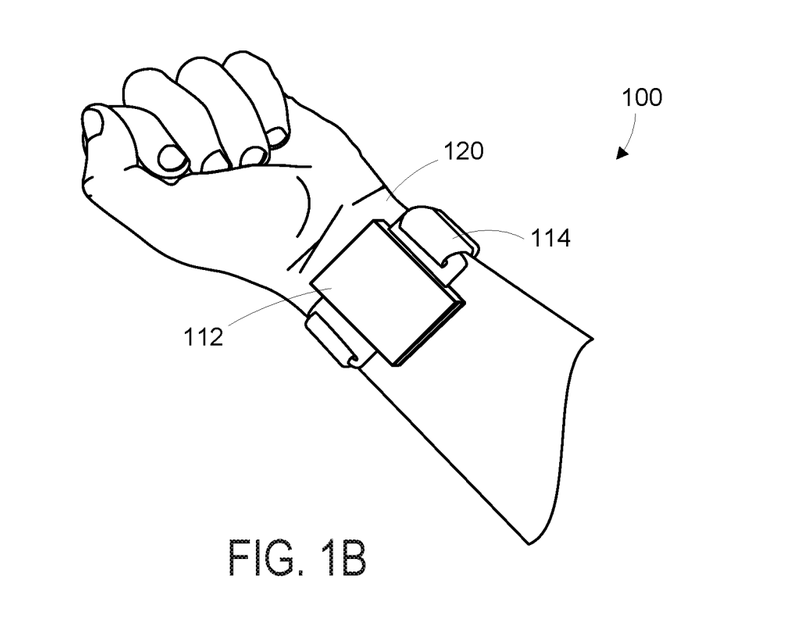
FIG. 1B illustrates an example wearable device including at least one ultrasonic transducer, shown mounted to a human wrist.
Figure 1C:
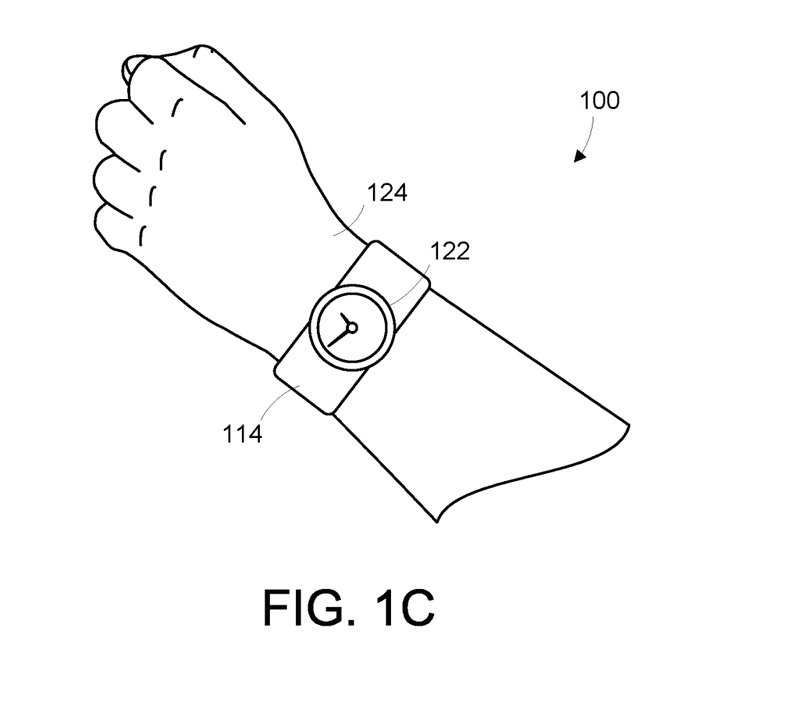
FIG. 1C illustrates an example wearable device including at least one ultrasonic transducer, shown mounted to a human wrist.

As shown in FIGS. 1B-1C, the wearable device 100 may in some examples be provided as a wrist-mounted device. The wrist-mounted device may be mounted to a wrist with a wristband or cuff, similar to a watch or bracelet, such that the housing 112 is positioned on the anterior side 120 of the wrist. An interface 122 may be provided on the mount 114 such that it is positioned on the posterior side 124 of the wearer's wrist. In some cases, the interface 122 may be an analog or digital watch face, as shown in FIG. 1C. The interface 122 may also be an electronic display capable of providing and receiving information from the wearer of the device. For example, the interface 122 may display or otherwise emit alerts, such as visual, sound or tactile alerts, to the wearer of the device. In other embodiments, both the housing 112 and the interface 122, if provided, may both be configured to be positioned on the posterior side of the wrist.

When mounted to a body surface, the wearable device 100 may be used to detect motion of one or more subsurface tendons. As will be described further below, the at least one transducer 110 may generate movement data based on the detected motion of the one or more subsurface tendons. The generated movement data may be, for example, interpreted as movement by one or more fingers of the wearer's hand. In some examples, the detected finger movement may be correlated with striking or selecting keys on a keyboard. In other examples, the detected finger movement may be correlated with other gestures such as swiping, scrolling, selecting, drawing, etc. Accordingly, the tendon movement detected by the one or more transducers 100 may be used to generate one or more inputs into a computing device. Additionally or alternatively, the device 100 may be configured to be mounted to other body surfaces proximate to one or more subsurface tendons, such as tendons of the elbow, shoulder, neck, feet, etc. Tendon movements detected from these other areas of the body may be interpreted as other gestures which may be used to generate inputs into a computing device.

Figure 2:
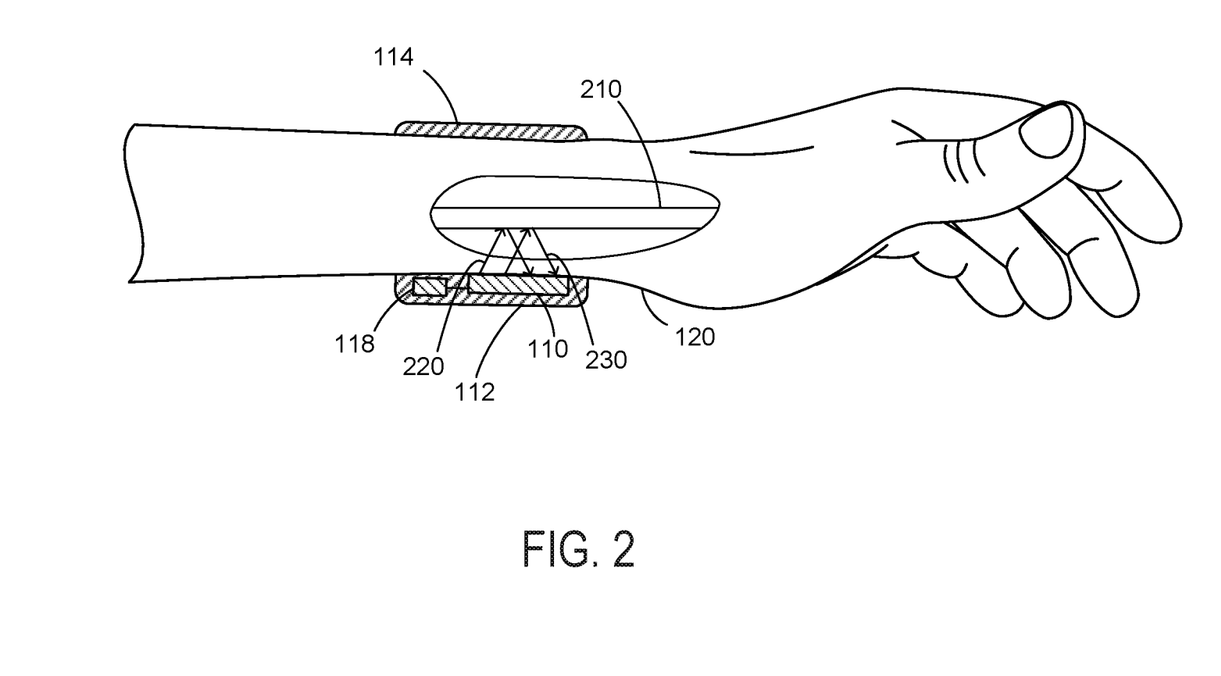
FIG. 2 is a partial cutaway view of an example wearable device including at least one ultrasonic transducer mounted to a human wrist.

FIG. 2 is a partial cutaway view illustrating a wearable device 100 mounted to a wrist proximate to one or more subsurface tendons 210. The housing 112, containing the one or more transducers 110, is positioned on the anterior side 120 of the wrist. In this example, the at least one ultrasonic transducer 110 may be configured to monitor the movement of each tendon in the carpal tunnel region that control finger movement. In operation, each of the at least one ultrasound transducers 110 emit ultrasound waves 220 into the wrist of the wearer. The echo waves 230 received back at the at least one ultrasound transducer 110 may be evaluated to determine, for example, a time interval or frequency shift between the emitted and received ultrasound waves to detect tendon movement.

The at least one ultrasonic transducer 110 can, in some embodiments, comprise an ultrasonic transducer array. For example, pulsed Doppler ultrasound may be used with a phased array of transducers. In one example, the array may be provided as a linear array having approximately 50 individual transducers, each of approximately 30 mm in length. The transducers may operate at approximately 8 MHz. The phase of the wave emitted by each transducer is shifted relative to each other to form an ultrasonic beam from the array (e.g., beamforming). Constructive interference from the phase-shifted waves emitted by each transducer causes certain directions to contain much more ultrasonic power than others. In one example, brightness variations in the resulting Doppler image are analyzed to identify tendons. The Doppler frequency shift detected from different parts of the device field of view is used to determine tendon movement. This data can be used in conjunction with data from existing anatomic templates to identify the source of movement, e.g., to identify which tendons of which fingers are moving.

Alternatively, the at least one ultrasonic transducer 110 may comprise a pair of transducers. In some embodiments, the at least one ultrasonic transducer 110 may comprise a pair of transducers for each tendon desired to be monitored. For example, where the wearable device 100 is provided as a wrist-mounted device, the at least one ultrasonic transducer 110 may include 5 pairs of transducers—one pair for the tendon(s) of each finger. Signal crosstalk occurring due to the width of the beam formed by each single pair of transducers can be overcome by a calibration procedure. In one example, a user may be instructed to move each finger on command and the pairs of transducers receive echo signals. The movement data generated from each pair of transducers is correlated with the instructed finger motion and a mapping that assigns how a combination of ultrasound signals indicates a specific movement may be developed. In operation, the Doppler frequency shift detected by the pairs of transducers is compared to the mapping to identify movement from a particular finger.

Figure 3:
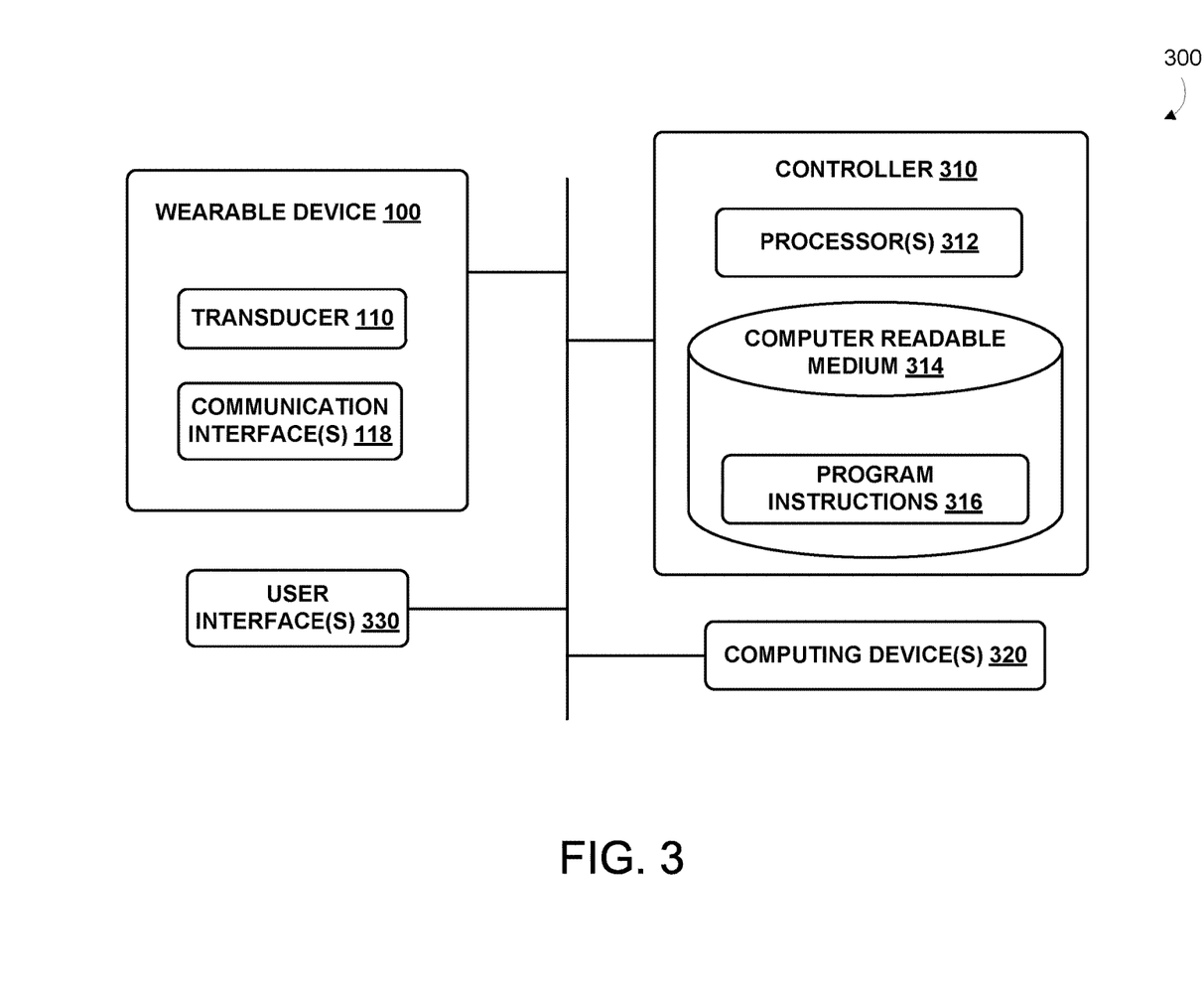
FIG. 3 is a block diagram of an example system, according to an example embodiment.

FIG. 3 illustrates a block diagram of a system 300 that includes a wearable device 100, having at least one ultrasonic transducer 110 and a communication interface 118, a controller 310 operably coupled to the at least one ultrasonic transducer 110, and one or more remote computing devices 320. The computing device(s) 320 may be any type of computing device capable of accepting one or more inputs. For example, the computing device may be a mobile phone, a smart phone, a personal computing device, a tablet, a wearable computing device (e.g., a smart watch, head-mountable display, etc.), a television, etc. The computing device input may be any input recognizable by the device or an application being run by the device. For example, a word processing system being run by a computing device 320 may recognize an alphanumeric character as an input. In some cases, the input may be configured to control a function of the computing device. For example, the input may be a swipe, scroll or select gesture.

The controller 310 may, in some embodiments, communicate with the computing device(s) 320 via a wireless connection, such as Bluetooth® radio technology, communication protocols described in IEEE 802.11 (including any IEEE 802.11 revisions), Cellular technology (such as GSM, CDMA, UMTS, EV-DO, WiMAX, or LTE), or Zigbee® technology. Additionally or alternatively, the controller 310 may communicate with the computing device(s) 320 via a wired connection such as a universal serial bus or parallel bus connection. In some cases, the controller 310 may be provided as part of a computing device 320. For example, the controller 310 may be provided, in whole or in part, as an application run on the computing device 320.

In some examples, the controller 310 may be provided as an integrated element of the wearable device 100. The controller 310 may, therefore, be coupled to the at least one ultrasonic transducer 110 by, for example, a wired connection. In this example, the communication interface 118 may be a wired serial bus such as a universal serial bus or a parallel bus. A wired connection may be a proprietary connection as well. Alternatively, the controller 310 may be external to the wearable device 100. In this example, the controller 310 may wirelessly communicate with the at least one transducer 110 via communication interface 118 using, for example, one of the wireless communication modes described above, among other possibilities.

The controller 310 may include a processor 312 in communication with a memory, such as a non-transitory computer-readable medium 314 that can include, without limitation, magnetic disks, optical disks, organic memory, and/or any other volatile (e.g. RAM) or non-volatile (e.g. ROM) storage system readable by the processor 312. The computer-readable medium 314 can include program instructions 316 for execution by the processor 312 to cause the controller 310 to perform processes specified by the instructions 316. For example, the program instructions 316 can cause controller 310 to operate the at least one ultrasonic transducer 110 to generate movement data based on detected movement of the at least one subsurface tendon. The controller 310 may, in one example, operate the at least one ultrasonic transducer to generate movement data by detecting a position of each of the one or more tendons based, at least in part, on a variation in image brightness and determining a Doppler frequency shift at the detected position of each of the one or more tendons. Further, the program instructions 316 can cause controller 310 to generate an input to computing device 320 based, at least in part, on the movement data generated by the at least one transducer 110. The controller 310 may determine whether to generate an input or determine which input, among a set of possible standard inputs, based, at least in part, on a comparison of the movement data to a set of standard movement data. The set of standard movement data, which may be stored on the non-transitory computer-readable medium 314, may have a set of standard computing device inputs associated therewith. The controller 310 may therefore recognize certain movements performed by the wearer of the device 100 by comparing the generated movement data to the set of standard movement data.

Further, the program instructions 316 can cause controller 310 perform certain calibration functions. The program instructions 316 may cause the controller 310 to provide an indication of a specified movement to be performed to a wearer of the device via a user interface 330. The user interface 330 may be provided as an integral component of either the controller 310 or the wearable device 100, or may be external to the controller 310 and the wearable device 100. For example, the user interface 330 may be generated by an application on a mobile computing device in communication with the controller 310. The specified movement indicated on the user interface 330 involves the at least one subsurface tendon and is associated with a specified input to the computing device. Based on a detected movement of the at least one subsurface tendon in response to the indication provided by the user interface, the controller 310 may generate calibration movement data. The controller 310 may generate a calibration map correlating the specified movement with the calibration movement data generated in response to the indication. After completing the calibration steps, the controller 310 may generate an input to the computing device based, at least in part, on a comparison between the movement data and the calibration map.

III. Example Methods

Figure 4:
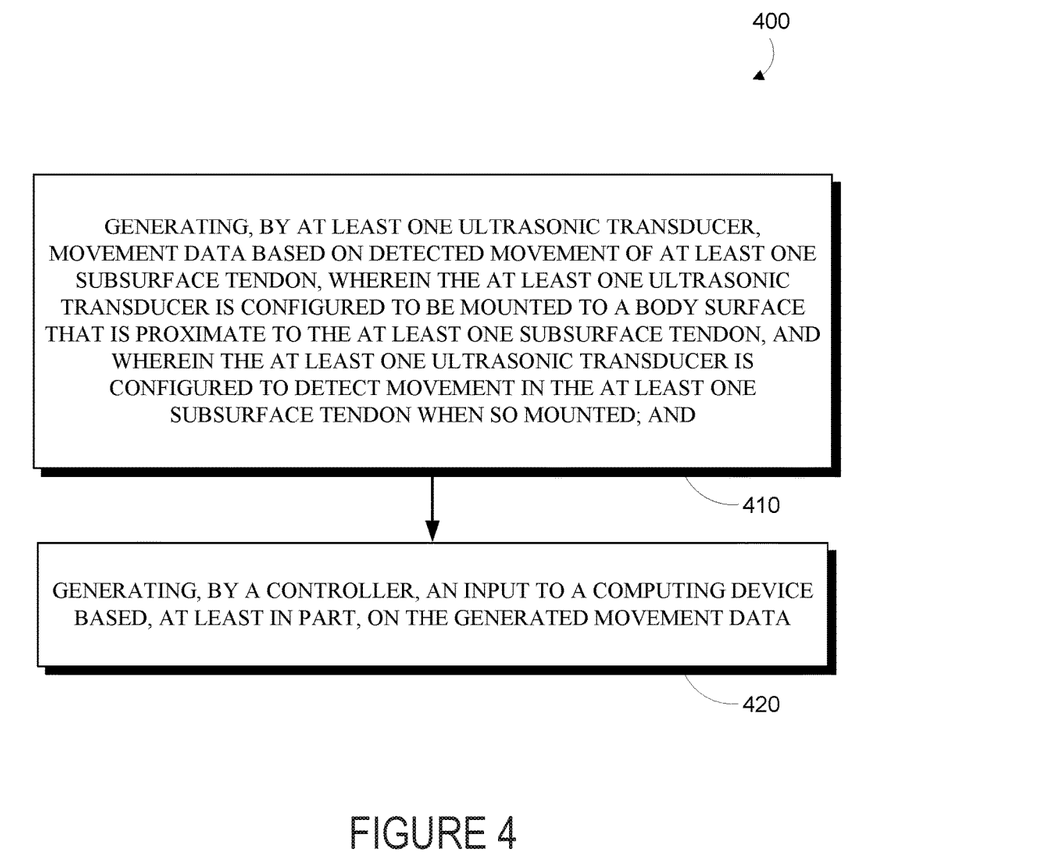
FIG. 4 is a flow chart of an example method, according to an example embodiment.

FIG. 4 is a flowchart of an example method 400 for generating an input to a computing device. The example methods described herein may be carried out by any system and device described herein, such as system 300. In a first step 410, movement data is generated by an ultrasonic transducer, such as transducer 110, based on detected movement of at least one subsurface tendon. The at least one ultrasonic transducer 110 is configured to be mounted to a body surface that is proximate to the at least one subsurface tendon. As described above, the ultrasonic transducer 110 may be provided as part of a wearable device configured to be mounted to a body surface, such as wearable device 100. The at least one ultrasonic transducer is configured to detect movement in the at least one subsurface tendon when mounted to a body surface. A controller, such as controller 310, generates an input to a computing device based, at least in part, on the generated movement data (420). The computing device, such as computing device 320, may be any electronic device with computing capabilities that is configured to accept at least one input. For example, the computing device 320 may be a smartphone. In one example, the controller may operate the at least one ultrasonic transducer to detect a position of each of the one or more tendons based, at least in part, on a variation in image brightness. The controller further generates movement data by determining a Doppler frequency shift at the detected position of each of the one or more tendons. The controller may generate the input to the computing device by comparing the generated movement data to standard movement data. The standard movement data is associated with one or more standard inputs configured to be recognized by the computing device.

In another example, the controller may provide an indication to a wearer of the device, via a user interface, of a specified movement to be performed. The specified movement involves the at least one subsurface tendon and is associated with a specified input to the computing device. Based on a detected movement of the at least one subsurface tendon in response to the indication, the controller generates calibration movement data. The controller further generates a calibration map correlating the specified movement with the calibration movement data generated in response to the indication. An input to the computing device may be generated by comparing the movement data to the calibration map.

IV. Conclusion

The present disclosure is not to be limited in terms of the particular embodiments described in this application, which are intended as illustrations of various aspects. Other embodiments can be utilized, and other changes can be made, without departing from the spirit or scope of the subject matter presented herein, as will be apparent to those skilled in the art. It will be readily understood that the aspects of the present disclosure, as generally described herein, and illustrated in the figures, can be arranged, substituted, combined, separated, and designed in a wide variety of different configurations, all of which are explicitly contemplated herein. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of example systems, devices, and methods with reference to the accompanying figures. In the figures, similar symbols typically identify similar components, unless context dictates otherwise. The example embodiments described herein and in the figures are not meant to be limiting. It should be understood that other embodiments can include more or less of each element shown in a given figure. Further, some of the illustrated elements can be combined or omitted. Yet further, an example embodiment can include elements that are not illustrated in the figures.

It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Reference is made herein to the accompanying figures, which form a part thereof. In the figures, similar symbols typically identify similar components, unless context dictates otherwise. Other embodiments may be utilized, and other changes may be made, without departing from the spirit or scope of the subject matter presented herein. The various aspects and embodiments disclosed herein are for purposes of illustration and are not intended to be limiting, with the true scope and spirit being indicated by the following claims.

What is claimed is:

1. A system, comprising:
   at least one ultrasonic transducer configured to be mounted to a body surface that is proximate to at least one subsurface tendon, wherein the at least one ultrasonic transducer is configured to detect movement of the at least one subsurface tendon when so mounted; and
   a controller operably coupled to the at least one ultrasonic transducer, and wherein the controller is configured to perform operations comprising:
      operating the at least one ultrasonic transducer to generate movement data based on detected movement of the at least one subsurface tendon, wherein operating the at least one ultrasonic transducer to generate movement data based on detected movement of the at least one subsurface tendon comprises: (i) detecting a position of each of the one or more tendons, and (ii) determining a Doppler frequency shift at the detected position of each of the one or more tendons; and
      generating an input to a computing device based, at least in part, on the generated movement data.

2. The system of claim 1, wherein the at least one ultrasonic transducer comprises an ultrasonic transducer array.

3. The system of claim 1, wherein
   detecting a position of each of the one or more tendons comprises detecting a position of each of the one or more tendons based, at least in part, on a variation in image brightness.

4. The system of claim 1, wherein the at least one ultrasonic transducer comprises at least one pair of ultrasonic transducers.

5. The system of claim 4, wherein the at least one ultrasonic transducer comprises a pair of ultrasonic transducers for each of the at least one subsurface tendon.

6. The system of claim 4, wherein operating the at least one ultrasonic transducer to generate movement data based on detected movement of the at least one subsurface tendon comprises:
providing an indication, via a user interface, of a specified movement to be performed, wherein the specified movement involves the at least one subsurface tendon, and wherein the specified movement is associated with a specified input to the computing device;
generating calibration movement data based on a detected movement of the at least one subsurface tendon in response to the indication; and
generating a calibration map correlating the specified movement with the calibration movement data generated in response to the indication.

7. The system of claim 6, wherein generating the input to the computing device comprises:
comparing the movement data to the calibration map.

8. The system of claim 1, wherein the input comprises an alphanumeric character.

9. The system of claim 1, wherein the input is configured to control a function of the computing device.

10. The system of claim 1, wherein generating the input to the computing device comprises:
comparing the generated movement data to standard movement data, wherein the standard movement data is associated with one or more standard inputs configured to be recognized by the computing device.

11. A method, comprising:
generating, by at least one ultrasonic transducer, movement data based on detected movement of at least one subsurface tendon, wherein the at least one ultrasonic transducer is configured to be mounted to a body surface that is proximate to the at least one subsurface tendon, and wherein the at least one ultrasonic transducer is configured to detect movement in the at least one subsurface tendon when so mounted, and wherein operating the at least one ultrasonic transducer to generate movement data based on detected movement of the at least one subsurface tendon comprises: (i) detecting a position of each of the one or more tendons, and (ii) determining a Doppler frequency shift at the detected position of each of the one or more tendons; and
generating, by a controller, an input to a computing device based, at least in part, on the generated movement data.

12. The method of claim 11, wherein
detecting a position of each of the one or more tendons comprises detecting a position of each of the one or more tendons based, at least in part, on a variation in image brightness.

13. The method of claim 11, wherein operating the at least one ultrasonic transducer to generate movement data based on detected movement of the at least one subsurface tendon comprises:
providing an indication, via a user interface, of a specified movement to be performed, wherein the specified movement involves the at least one subsurface tendon, and wherein the specified movement is associated with a specified input to the computing device;
generating calibration movement data based on a detected movement of the at least one subsurface tendon in response to the indication; and
generating a calibration map correlating the specified movement with the calibration movement data generated in response to the indication.

14. The method of claim 13, wherein generating the input to the computing device comprises:
comparing the movement data to the calibration map.

15. The method of claim 11, wherein generating the input to the computing device comprises:
comparing the generated movement data to standard movement data, wherein the standard movement data is associated with one or more standard inputs configured to be recognized by the computing device.

16. A non-transitory computer readable medium having stored therein instructions executable by a processor to cause a controller to perform operations comprising:
operating at least one ultrasonic transducer to generate movement data based on detected movement of at least one subsurface tendon, wherein the at least one ultrasonic transducer is configured to be mounted to a body surface that is proximate to the at least one subsurface tendon, and wherein the at least one ultrasonic transducer is configured to detect movement in the at least one subsurface tendon when so mounted, and wherein operating the at least one ultrasonic transducer to generate movement data based on detected movement of the at least one subsurface tendon comprises: (i) detecting a position of each of the one or more tendons based, at least in part, on a variation in image brightness, and (ii) determining a Doppler frequency shift at the detected position of each of the one or more tendons; and
generating an input to a computing device based, at least in part, on the generated movement data.

17. The non-transitory computer readable medium of claim 16, wherein
detecting a position of each of the one or more tendons comprises detecting a position of each of the one or more tendons based, at least in part, on a variation in image brightness.

18. The non-transitory computer readable medium of claim 16, wherein operating the at least one ultrasonic transducer to generate movement data based on detected movement of the at least one subsurface tendon comprises:
providing an indication, via a user interface, of a specified movement to be performed, wherein the specified movement involves the at least one subsurface tendon, and wherein the specified movement is associated with a specified input to the computing device;
generating calibration movement data based on a detected movement of the at least one subsurface tendon in response to the indication; and
generating a calibration map correlating the specified movement with the calibration movement data generated in response to the indication.

19. The non-transitory computer readable medium of claim 18, wherein generating the input to the computing device comprises:
comparing the movement data to the calibration map.

20. The non-transitory computer readable medium of claim 16, wherein generating the input to the computing device comprises:
comparing the generated movement data to standard movement data, wherein the standard movement data is associated with one or more standard inputs configured to be recognized by the computing device.

* * * * *